United States Patent
Bayarmagnai et al.

(10) Patent No.: US 11,292,780 B2
(45) Date of Patent: Apr. 5, 2022

(54) PROCESS FOR PREPARING CYCLIC CARBONATES

(71) Applicant: BASF SE, Ludwigshafen am Rhein (DE)

(72) Inventors: Bilguun Bayarmagnai, Heidelberg (DE); Thomas Schaub, Ludwigshafen (DE); Verena Mormul, Ludwigshafen (DE); Peter Rudolf, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 153 days.

(21) Appl. No.: 16/634,255

(22) PCT Filed: Aug. 14, 2018

(86) PCT No.: PCT/EP2018/072014
§ 371 (c)(1),
(2) Date: Jan. 27, 2020

(87) PCT Pub. No.: WO2019/034648
PCT Pub. Date: Feb. 21, 2019

(65) Prior Publication Data
US 2020/0369640 A1    Nov. 26, 2020

(30) Foreign Application Priority Data
Aug. 14, 2017 (EP) ..................................... 17186136

(51) Int. Cl.
| | |
|---|---|
| *C07D 317/40* | (2006.01) |
| *B01J 31/22* | (2006.01) |
| *C08F 124/00* | (2006.01) |
| *H01M 10/0567* | (2010.01) |

(52) U.S. Cl.
CPC ........ *C07D 317/40* (2013.01); *B01J 31/2282* (2013.01); *C08F 124/00* (2013.01); *H01M 10/0567* (2013.01); *H01M 2300/0025* (2013.01)

(58) Field of Classification Search
CPC ............................ C07D 317/40; C07D 317/34
USPC ................................................. 549/296, 295
See application file for complete search history.

(56) References Cited

U.S. PATENT DOCUMENTS

| | | | |
|---|---|---|---|
| 6,639,114 | B2 | 10/2003 | Ahlers et al. |
| 10,604,500 | B2 | 3/2020 | Licht et al. |
| 2013/0059178 | A1 | 3/2013 | Ihara et al. |

FOREIGN PATENT DOCUMENTS

WO    WO 2011/157671 A1    12/2011

OTHER PUBLICATIONS

Tang, X. et al.: Polystyrene-supported N-heterocyclic Carbene-silver complexes as robust and efficient catalysts for the reaction of Carbon dioxide and propargylic alcohols. Adv. Synthesis & Catalysis, vol. 355, pp. 2019-2028, 2013.*
International Preliminary Report on Patentability dated Feb. 18, 2020 in PCT/EP2018/072014 filed Aug. 14, 2018, 6 pages.
Andrea Buzas, et al., "Gold(I)-Catalyzed Formation of 5-Methylene-1,3-oxazolidin-2-ones", Synlett, vol. 17, 2006, pp. 2727-2730.
Nicola Della CA, et al., "Effective Guanidine-Catalyzed Synthesis of Carbonate and Carbamate Derivatives from Propargyl Alcohols in Supercritical Carbon Dioxide" Advanced Synthesis and Catalysis, vol. 353, Issue 1, Jan. 20, 2011, pp. 133-146.
Pierre De Fremont, et al., "Carbenes: Synthesis, Properties, and Organometallic Chemistry" Coordination Chemistry Reviews, vol. 253, 2009, pp. 862-892.
Yoshio Inoue, et al., "Cobaltocene-Catalyzed Reaction of Carbon Dioxide with Propargyl Alcohols" Bulletin of the Chemical Society of Japan, vol. 60, Issue 3, Mar. 1987, pp. 1204-1206.
Hak-Soo Kim, et al., "Catalytic Formation of Carbamates and Cyclic Carbonates by Copper Complex of 2,5,19,22-tetraaza[6,6](1,1')ferrocenophane-1,5-diene X-ray Crystal Structure of [Cu(1)]PF6" Journal of Organometallic Chemistry, vol. 545-546, 1997, pp. 337-344.
David V. Partyka, et al., "Facile Synthesis of (Phosphine)- and (N-heterocyclic Carbene) Gold(I) and Silver(I) Azide Complexes" Organometallics, vol. 28, Issue 3, Jan. 6, 2009, pp. 795-801.

(Continued)

*Primary Examiner* — Charanjit Aulakh
(74) *Attorney, Agent, or Firm* — Grüneberg and Myers PLLC

(57) ABSTRACT

The present invention relates to a process for preparing cyclic carbonates of formula Ia or Ib or mixtures thereof (Ia) (Ib) comprising the process step: a) reacting a propargylic alcohol of formula II (II) with carbon dioxide in the presence of at least one transition metal catalyst TMC1, which comprises a transition metal selected from metals of groups 10, 11 and 12 of the periodic table of the elements according to IUPAC and at least one bulky ligand.

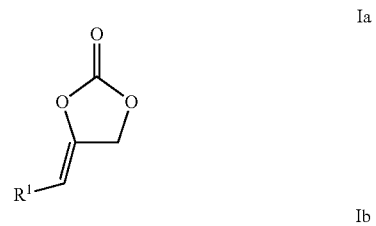

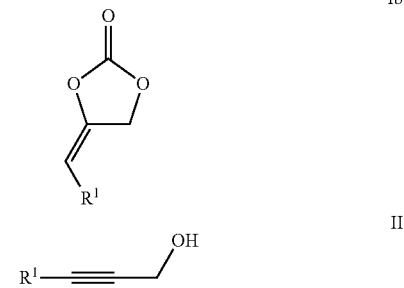

16 Claims, No Drawings

(56) References Cited

OTHER PUBLICATIONS

Barry M. Trost, et al., "Synthesis of 4-Methylene-1,3-Dioxolan-2-one, a Bifunctional Cyclic Carbonate" Journal of Organic Chemistry, vol. 48, Issue 19, Sep. 1, 1983, pp. 3346-3347.
Wataru Yamada, et al., "Silver-Catalyzed Incorporation of Carbon Dioxide into Propargylic Alcohols" European Journal of Organic Chemistry, vol. 2007, Issue 16, May 10, 2007, pp. 2604-2607.
Hirofumi Yamamoto, et al., "Hg(OTf)2-Catalyzed Cyclization of alkynyl tert-butylcarbonate Leading to Cyclic Enol Carbonate" Tetrahedron Letters, vol. 47, Issue 47, Nov. 20, 2006, pp. 8369-8373.
International Search Report dated Sep. 24, 2018 in PCT/EP2018/072014 filed on Aug. 14, 2018, 3 pages.
Buzas et al., "Gold-catalyzed rearrangement of propargylic tert-butyl carbonates," Elsevier, Tetrahedron, vol. 65, No. 9, 2009, pp. 1889-1901, DOI: 10.1016/j.tet.2008.11.108, XP055135539.
Qi. et al., "Efficient Synthesis of β-Oxoalkyl Carbamates from Carbon Dioxide, Internal Propargylic Alcohols, and Secondary Amines Catalyzed by Silver Salts and DBU," Synthesis, No. 9, 2010, pp. 1433-1440, DOI: 10.1055/s-0029-1218675, XP-002775643.

\* cited by examiner

PROCESS FOR PREPARING CYCLIC CARBONATES

The present invention relates to a process for preparing cyclic carbonates of formula Ia or Ib or mixtures thereof

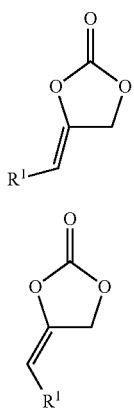

comprising the process step:
a) reacting a propargylic alcohol of formula II

with carbon dioxide in the presence of at least one transition metal catalyst TMC1, which comprises a transition metal selected from metals of groups 10, 11 and 12 of the periodic table of the elements according to IUPAC and at least one bulky ligand.

Exo-vinylene carbonates are valuable compounds, especially for the use in electrolytes for batteries as described in US 2013/0059178 A1 or as monomers in polymer applications as described in WO 2011/157671 A1. Exo-Vinylene carbonates with substituents in the 4,4-position are available via the reaction of secondary or tertiary propargylic alcohols with $CO_2$ using different catalysts like metals or bases.

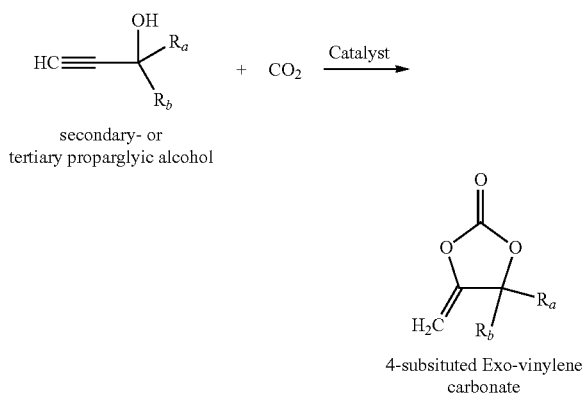

None of the protocols, which are described in the literature, like the Silver-, Copper-, Cobalt- or guanidine catalyzed cyclisations could until now be applied to the conversion of simple primary propargylic alcohols with $CO_2$ towards the simple Exo-vinylene carbonates with two hydrogens in the 4,4-positions.

In Eur. J Org. Chem. 2007, 2604-2607 the silver-catalyzed incorporation of carbon dioxide into propargylic alcohol is reported, where AgOAc in combination with DBU is the catalyst system. This catalyst system worked well for the cyclisation of tertiary propargylic alcohols, but the method was not applicable to primary or secondary propargylic alcohols for their conversion into the corresponding cyclic products.

In Journal of Organometallic Chemistry, 1997, 545-546, 337-344, a Cu-catalyzed cyclisation of propargylic alcohols with $CO_2$ is reported. The copper catalyst, which comprised a tetradentate imine ligand was used in combination with different amine bases. These catalysts worked well for the cyclisation of tertiary propargylic alcohols, but no cyclisation product was formed from primary propargylic alcohol.

In the attempts for the guanidine-catalyzed cyclisation of propargylic alcohols with $CO_2$ reported in Advanced Synthesis and Catalysis, 2011, 353, 133-146, no metal catalyst was added. These catalysts worked well for the cyclisation of tertiary- and secondary propargylic alcohols, but no Exo-vinylenecarbonate from primary propargylic alcohol was formed under these conditions.

In the attempts for the Cobalt-catalyzed cyclisation of propargylic alcohols with $CO_2$ reported in Bulletin of the Chemical Society of Japan, 1987, 60, 1204-1206, $PPh_3$ was added as the donor ligand in combination with $NEt_3$ as the base. This catalyst worked well for the cyclisation of tertiary propargylic alcohols, but no Exo-vinylene carbonate from primary propargylic alcohol was formed under these conditions.

In the prior art, the only reasonable synthetic approach to the 4-methylene-1,3-dioxolan-2-one, the simplest Exo-vinylene carbonate, is the Gold- or Mercury catalyzed cyclisation of propargylic tert-butylcarbonates which is described in Synlett, 2006, 17, 2727-2730 and in Tetrahedron Letters, 2006, 47, 8369-8373.

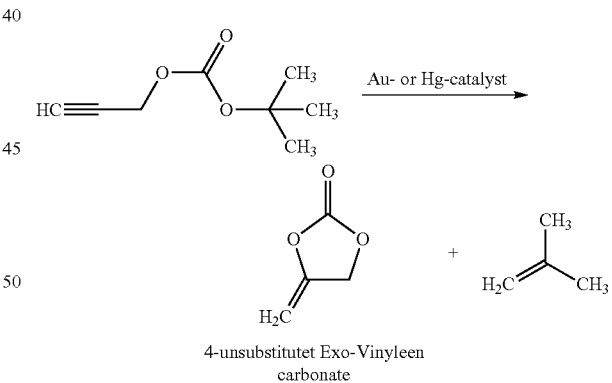

One disadvantage of this route is, that the propargylic tert-butylcarbonate must be prepared first from propargylic alcohol and the relatively expensive BOC-anhydride.

Another disadvantage of the cyclisation of the propargylic tert-butlycarboante is, that the other tBu group is released as Isobutene and therefore a byproduct is formed, which must be disposed or recycled.

Another route towards 4-methylene-1,3-dioxolan-2-one is described in J. Org. Chem. 1983, 48(19), 3346-3347. This method starts from a chlorinated glycerol derivative and uses PhSeNa as reagent. This route does not allow commercial production of the product.

Accordingly, it is an object of the invention to provide a more economic process for preparing cyclic carbonates from primary propargylic alcohols and $CO_2$, preferably directly from primary propargylic alcohols and $CO_2$.

This object is achieved by a process for preparing cyclic carbonates of formula Ia or Ib or mixtures thereof

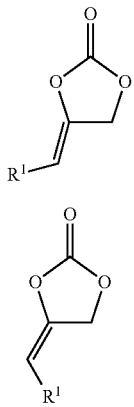

wherein
$R^1$ is hydrogen or an organic radical having from 1 to 40 carbon atoms,
comprising the process step:
a) reacting a propargylic alcohol of formula II

wherein $R^1$ has the same meaning as in formula Ia or Ib, with carbon dioxide in the presence of at least one transition metal catalyst TMC1, which comprises a transition metal selected from metals of groups 10, 11 and 12 of the periodic table of the elements according to IUPAC, preferably selected from Cu, Ag and Au, more preferably Ag, and at least one bulky ligand selected from the group of ligands consisting of compounds of formula III and compounds of formula IV, preferably compounds of formula III,

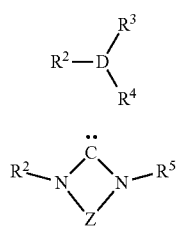

wherein
D is P, As or Sb, preferably P or As, in particular P,
$R^2$ is an organic radical having from 1 to 40 carbon atoms, preferably from 2 to 40 carbon atoms, preferably comprising at least one cyclic ring, more preferably, in formula III $R^2$ is a $C_3$ to $C_{40}$ cycloalkyl radical, a $C_2$ to $C_{40}$ heterocycloalkyl radical, a $C_6$ to $C_{40}$ aryl radical, a $C_2$ to $C_{40}$ heteroaromatic radical, a $C_3$ to $C_{40}$ cycloalkoxy radical, a $C_2$ to $C_{40}$ heterocycloalkoxy radical, a $C_6$ to $C_{40}$ aryloxy radical or a $C_2$ to $C_{40}$ hetaryloxy radical, in particular a $C_6$ to $C_{40}$ aryl radical or a $C_2$ to $C_{40}$ heteroaromatic radical,
$R^3$, $R^4$ are identical or different, and are each an organic radical having from 1 to 40 carbon atoms, and,
$R^5$ is an organic radical having from 1 to 40 carbon atoms or is identical to $R^2$,
and
Z is a divalent bridging group selected from $-CR^7=CR^8-$, $-CR^7=N-$, $-CR^7R^9-CR^8R^{10}-$ and $-CR^7R^9-CR^8R^{10}-CR^{11}R^{12}-$, wherein $R^7$, $R^8$, $R^9$, $R^{10}$, $R^{11}$ and $R^{12}$ are independently from each other hydrogen or as defined as $R^5$ or two adjacent radicals $R^7$ and $R^8$ and/or $R^{10}$ and $R^{11}$ together with the atoms connecting them form a monocyclic or polycyclic, substituted or unsubstituted, aliphatic or aromatic ring system which has from 4 to 40 carbon atoms and can also comprise at least one heteroatom selected from the group consisting of the elements Si, Ge, N, P, O and S.

In one embodiment of the present invention, the inventive process is characterized in that
D is P,
$R^2$ is a $C_3$ to $C_{40}$ cycloalkyl radical, a $C_2$ to $C_{40}$ heterocycloalkyl radical, a $C_6$ to $C_{40}$ aryl radical or a $C_2$ to $C_{40}$ heteroaromatic radical, preferably a $C_6$ to $C_{40}$ aryl radical or a $C_2$ to $C_{40}$ heteroaromatic radical, wherein $R^2$ is substituted in at least one of the two ortho positions relative to P or N with a radical $R^6$, which is an organic radical having from 1 to 40 carbon atoms, a halogen, in particular Cl or Br, hydroxy, $SO_3H$ or nitro or wherein $R^6$ together with an adjacent radical substituting $R^2$ in the meta position forms together with the atoms connecting them a monocyclic or polycyclic, substituted or unsubstituted, aliphatic or aromatic ring system, which has from 4 to 40 carbon atoms and can also comprise at least one heteroatom selected from the group consisting of the elements Si, Ge, N, P, O and S, preferably N and O,
$R^3$, $R^4$, $R^5$ and Z are defined as described above.

The substituents according to the present invention are, unless restricted further, defined as follows:

The term "organic radical having from 1 to 40 carbon atoms" as used in the present text refers to, for example, $C_1$-$C_{40}$-alkyl radicals, $C_1$-$C_{10}$-fluoroalkyl radicals, $C_1$-$C_{12}$-alkoxy radicals, saturated $C_3$-$C_{20}$-heterocyclic radicals, $C_6$-$C_{40}$-aryl radicals, $C_2$-$C_{40}$-heteroaromatic radicals, $C_6$-$C_{10}$-fluoroaryl radicals, $C_6$-$C_{10}$-aryloxy radicals, silyl radicals having from 3 to 24 carbon atoms, $C_2$-$C_{20}$-alkenyl radicals, $C_2$-$C_{20}$-alkynyl radicals, $C_7$-$C_{40}$-arylalkyl radicals or $C_8$-$C_{40}$-arylalkenyl radicals. An organic radical is in each case derived from an organic compound. Thus, the organic compound methanol can in principle give rise to three different organic radicals having one carbon atom, namely methyl ($H_3C-$), methoxy ($H_3C-O-$) and hydroxymethyl ($HOC(H_2)-$). Therefore, the term "organic radical having from 1 to 40 carbon atoms" comprises beside alkoxy radicals for example also dialkylamino radicals, monoalkylamino radicals or alkylthio radicals.

In the present description, the term radical is used interchangeably with the term group, when defining the variables $R^x$ in the presented formulas.

The term "alkyl" as used in the present text encompasses linear or singly or multiply branched saturated hydrocarbons which can also be cyclic. Preference is given to a $C_1$-$C_{18}$-alkyl radical such as methyl, ethyl, n-propyl, n-butyl, n-pentyl, n-hexyl, n-heptyl, n-octyl, n-nonyl, n-decyl, cyclopentyl, cyclohexyl, isopropyl, isobutyl, isopentyl, isohexyl, sec-butyl or tert-butyl The term "alkenyl" as used in the present text encompasses linear or singly or multiply branched hydrocarbons having one or more C—C double bonds which can be cumulated or alternating.

The term "saturated heterocyclic radical" as used in the present text refers to, for example, monocyclic or polycyclic, substituted or unsubstituted aliphatic or partially unsaturated hydrocarbon radicals in which one or more carbon atoms, CH groups and/or $CH_2$ groups have been replaced by heteroatoms which are preferably selected from the group consisting of the elements O, S, N and P. Preferred examples of substituted or unsubstituted saturated heterocyclic radicals are pyrrolidinyl, imidazolidinyl, pyrazolidinyl, piperidyl, piperazinyl, morpholinyl, tetrahydrofuranyl, tetrahydropyranyl, tetrahydrothiophenyl and the like, and also methyl-, ethyl-, propyl-, isopropyl- and tert-butyl-substituted derivatives thereof.

The term "aryl" as used in the present text refers to, for example, aromatic and optionally fused polyaromatic hydrocarbon radicals which may be monosubstituted or polysubstituted by linear or branched $C_1$-$C_{18}$-alkyl, $C_1$-$C_{18}$-alkoxy, $C_2$-$C_{10}$-alkenyl or halogen, in particular fluorine. Preferred examples of substituted and unsubstituted aryl radicals are, in particular, phenyl, pentafluorophenyl, 4-methylphenyl, 4-ethylphenyl, 4-n-propylphenyl, 4-isopropylphenyl, 4-tert-butylphenyl, 4-methoxyphenyl, 1-naphthyl, 9-anthryl, 9-phenanthryl, 3,5-dimethylphenyl, 3,5-di-tert-butylphenyl or 4-trifluoromethylphenyl.

The term "heteroaromatic radical" as used in the present text refers to, for example, aromatic hydrocarbon radicals in which one or more carbon atoms or CH groups have been replaced by nitrogen, phosphorus, oxygen or sulfur atoms or combinations thereof. These may, like the aryl radicals, optionally be monosubstituted or polysubstituted by linear or branched $C_1$-$C_{18}$-alkyl, $C_2$-$C_1$-alkenyl or halogen, in particular fluorine. Preferred examples are furyl, thienyl, pyrrolyl, pyridyl, pyrazolyl, imidazolyl, oxazolyl, thiazolyl, pyrimidinyl, pyrazinyl and the like, and also methyl-, ethyl-, propyl-, isopropyl- and tert-butyl-substituted derivatives thereof.

The term "arylalkyl" as used in the present text refers to, for example, aryl-comprising substituents whose aryl radical is linked via an alkyl chain to the remainder of the molecule. Preferred examples are benzyl, substituted benzyl, phenethyl, substituted phenethyl and the like.

The terms fluoroalkyl and fluoroaryl mean that at least one hydrogen atom, preferably more than one and at most all hydrogen atoms, of the corresponding radical have been replaced by fluorine atoms. Examples of preferred fluorine-comprising radicals are trifluoromethyl, 2,2,2-trifluoroethyl, pentafluorophenyl, 4-trifluoromethylphenyl, 4-perfluoro-tert-butylphenyl and the like.

$R^1$ in formulas Ia, Ib and II is hydrogen or an organic radical having from 1 to 40 carbon atoms, preferably hydrogen, acyclic or cyclic, substituted or unsubstituted $C_1$-$C_{10}$-alkyl, substituted or unsubstituted $C_6$-$C_{10}$-aryl or substituted or unsubstituted $C_7$-$C_{12}$-arylalkyl, in particular hydrogen or hydroxymethyl or a corresponding ester or carbonate thereof, in particular acetoxy-methylene (—$CH_2$OC(O)$CH_3$), formyloxy-methylene —$CH_2$OC(O)H or —$CH_2$OC(O)$OCH_3$.

In one embodiment of the present invention, the inventive process is characterized in that $R^1$ is hydrogen, hydroxymethyl (—$CH_2$OH), acetoxy-methylene (—$CH_2$OC(O)$CH_3$), formyloxy-methylene (—$CH_2$OC(O)H) or —$CH_2$OC(O)$OCH_3$.

For the avoidance of doubt, the term "propargylic alcohol of formula II" as used in the present description is not restricted to 2-Propyn-1-ol alone but it describes all compounds, which comprise the prop-2-yn-1-ol group.

In the process of the invention, the propargylic alcohol of formula II is reacted with carbon dioxide in the presence of at least one transition metal catalyst TMC1. Transition metal catalyst TMC1 comprises a transition metal selected from metals of groups 10, 11 and 12 of the periodic table of the elements according to IUPAC, such as Ni, Pd, Pt, Cu, Ag, Au, Zn, Cd and Hg, preferably selected from Cu, Ag and Au, more preferably selected from Cu or Ag, in particular Ag.

In one embodiment of the present invention, the inventive process is characterized in that the transition metal of transition metal catalyst TMC1 is Ag The transition metal catalyst TMC1 of the process of the invention can be employed in the form of a preformed metal complex which comprises a transition metal and at least one bulky ligand selected from the group of ligands consisting of compounds of formula III and compounds of formula IV, preferably compounds of formula III, as shown above. Alternatively, the transition metal catalyst TMC1 is formed in situ in the reaction medium by combining a metal compound, herein also termed pre-catalyst, which does not comprise any bulky ligand, with one or more suitable bulky ligand to form a catalytically active metal complex, the transition metal catalyst TMC1, in the reaction medium. In case the bulky ligand is a N-heterocyclic carbene ligand (NHC-ligand) of formula IV, it is also possible that the transition metal catalyst TMC1 is formed in situ in the reaction medium by combining a pre-catalyst with one or more NHC-precursor, in particular the protonated form of a NHC-ligand, which is in situ converted to the corresponding NHC-ligand of formula IV, to form a catalytically active metal complex in the reaction medium.

In one embodiment of the present invention, the inventive process is characterized in that the transition metal catalyst TMC1 is prepared in situ by using a transition metal compound, which does not comprise any bulky ligand, the compound of formula III or formula IV as bulky ligand or the protonated form of the compound of formula IV represented by formula V,

V wherein $R^2$, $R^5$ and Z are defined as described above and $X^-$ is an anion equivalent, together with a base.

Suitable bases for deprotonating the protonated form of different NHC ligands according to formula V are described by de Frémont et al., Coordination Chemistry Reviews 253 (2009) 876 to 881. The deprotonation of the protonated forms of NHC ligands can be carried out in ammonia or in non-protic solvents such as THF or ethers. The deprotonation requires anhydrous conditions and the use of strong bases, with $pK_a$ values above 14. Usually, potassium or sodium hydride with a catalytic amount of tert-butoxide is employed, but tert-butoxide itself, lithium aluminum hydride, n-butyllithium, MeLi, t-BuLi, potassium hexamethyldisilazide (KHMDS) and 1,8-diazabicyclo[5.4.0]undec-7-ene (DBU) are also efficient alternatives.

Suitable pre-catalysts are selected from neutral metal complexes, oxides and salts of metals of groups 10, 11 and 12 of the periodic table of the elements. Preferred pre-catalysts are selected from metal complexes, oxides and salts of copper, silver and gold, in particular silver.

Silver compounds that are useful as pre-catalyst are, for example Ag(OAc), AgF, $AgNO_3$, silver trifluoroacetate, $Ag_2O$, $Ag_2CO_3$.

In one embodiment of the present invention, the inventive process is characterized in that the transition metal compound, also called pre-catalyst, is selected from AgOAc, AgF, $Ag_2O$ and $Ag_2CO_3$.

In addition to the transition metal, the transition metal catalyst TMC1 comprises at least one bulky ligand selected from the group of ligands consisting of compounds of formula III and compounds of formula IV, preferably compounds of formula III.

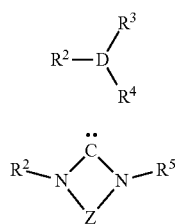

III

In case the bulky ligand is a compound of formula III,

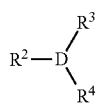

III the variables are preferably defined as follows:
D is P, As or Sb, preferably P or As, in particular P,
$R^2$ is an organic radical having from 1 to 40 carbon atoms, preferably from 2 to 40 carbon atoms, preferably comprising at least one cyclic ring,
  more preferably $R^2$ is a $C_3$ to $C_{40}$ cycloalkyl radical, a $C_2$ to $C_{40}$ heterocycloalkyl radical, a $C_6$ to $C_{40}$ aryl radical, a $C_2$ to $C_{40}$ heteroaromatic radical, a $C_3$ to $C_{40}$ cycloalkoxy radical, a $C_2$ to $C_{40}$ heterocycloalkoxy radical, a $C_6$ to $C_{40}$ aryloxy radical, a $C_2$ to $C_{40}$ hetaryloxy radical,
  even more preferably $R^2$ is a $C_3$ to $C_{40}$ cycloalkyl radical, a $C_2$ to $C_{40}$ heterocycloalkyl radical, a $C_6$ to $C_{40}$ aryl radical or a $C_2$ to $C_{40}$ heteroaromatic radical, preferably a $C_6$ to $C_{40}$ aryl radical or a $C_2$ to $C_{40}$ heteroaromatic radical, wherein $R^2$ is substituted in at least one of the two ortho positions relative to D with a radical $R^6$, which is an organic radical having from 1 to 40 carbon atoms, preferably a $C_6$ to $C_{40}$ aryl radical, a $C_1$ to $C_{10}$ alkoxy radical or a $C_2$ to $C_{12}$ dialkyl amino radical or wherein $R^6$ together with an adjacent radical substituting $R^2$ in the meta position forms together with the atoms connecting them a monocyclic or polycyclic, substituted or unsubstituted, aliphatic or aromatic ring system, which has from 4 to 40 carbon atoms and can also comprise at least one heteroatom selected from the group consisting of the elements Si, Ge, N, P, O and S, preferably N, O and S,
and
$R^3$, $R^4$ are identical or different, preferably identical, and are each an organic radical having from 1 to 40 carbon atoms, preferably $C_3$ to $C_{20}$ cyclic or acyclic alkyl, in particular tert.-butyl or cyclohexyl, or $C_6$ to $C_{14}$ aryl, in particular phenyl.

In case the bulky ligand is a compound of formula IV,

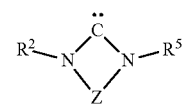

IV the variables are preferably defined as follows:
$R^2$ is an organic radical having from 1 to 40 carbon atoms, preferably from 2 to 40 carbon atoms, preferably comprising at least one cyclic ring, more preferably $R^2$ is a $C_6$ to $C_{40}$ aryl radical or a $C_2$ to $C_{40}$ heteroaromatic radical, preferably wherein $R^2$ is substituted in at least one of the two ortho positions relative to N with a radical $R^6$, which is an organic radical having from 1 to 40 carbon atoms, preferably a $C_1$ to $C_{10}$ alkyl radical, in particular isopropyl,
$R^5$ is an organic radical having from 1 to 40 carbon atoms or is identical to $R^2$, preferably $R^5$ is identical to $R^2$,
and
Z is a divalent bridging group selected from $-CR^7=CR^8-$, $-CR^7=N-$, $-CR^7R^9-CR^8R^{10}-$ and $-CR^7R^9-CR^8R^{10}-CR^{11}R^{12}-$, preferably $-CR^7=CR^8-$ and $-CR^7R^9-CR^8R^{10}-$, wherein $R^7$, $R^8$, $R^9$, $R^{10}$, $R^{11}$ and $R^{12}$ are independently from each other hydrogen or as defined as $R^5$, preferably H, or two adjacent radicals $R^7$ and $R^8$ and/or $R^{10}$ and $R^{11}$ together with the atoms connecting them form a monocyclic or polycyclic, substituted or unsubstituted, aliphatic or aromatic ring system which has from 4 to 40 carbon atoms and can also comprise at least one heteroatom selected from the group consisting of the elements Si, Ge, N, P, O and S.

In one embodiment of the present invention, the inventive process is characterized in that the bulky ligand is a compound of formula III.

In one embodiment of the present invention, the inventive process is characterized in that the bulky ligand is a compound of formula III

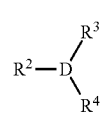

III wherein the variables are defined as follows:
D is P,
$R^2$ is a $C_6$ to $C_{40}$ aryl radical or a $C_2$ to $C_{40}$ heteroaromatic radical, wherein $R^2$ is substituted in at least one of the two ortho positions relative to D with a radical $R^6$, which is a $C_6$ to $C_{40}$ aryl radical, a $C_1$ to $C_{10}$ alkoxy radical, in particular methoxy, ethoxy, isopropoxy or cyclohexyloxy, or a $C_2$ to $C_{12}$ dialkyl amino radical, in particular dimethyl amino, diethyl amino, di-isopropyl amino, N-morpholinyl or N-piperidyl, or wherein $R^6$ together with an adjacent radical substituting $R^2$ in the meta position forms together with the atoms connecting them a monocyclic or polycyclic, substituted or unsubstituted, aliphatic or aromatic ring system, which has from 4 to 40 carbon atoms and can also comprise at least one heteroatom selected from the group consisting of the elements Si, Ge, N, P, O and S, preferably N, O and S, and $R^3$, $R^4$ are identical or different, preferably identical, and are each an organic radical having from 1 to 40 carbon atoms, preferably $C_3$ to $C_{20}$ cyclic or acyclic alkyl, in particular tert.-butyl, adamantyl or cyclohexyl, or $C_6$ to $C_{14}$ aryl, in particular phenyl.

In one embodiment of the present invention, the inventive process is characterized in that the bulky ligand is selected from a compound of formulas A to P and mixtures thereof, preferably a compound of formulas A to D and mixtures thereof.

A

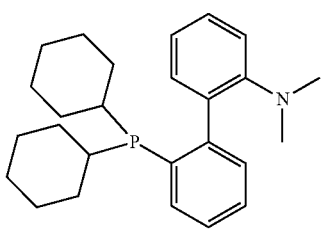

B

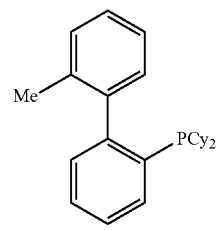

C

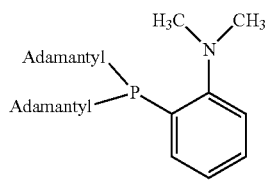

D

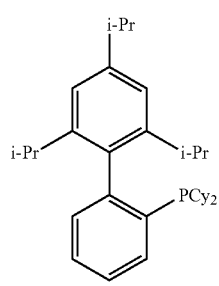

-continued

E

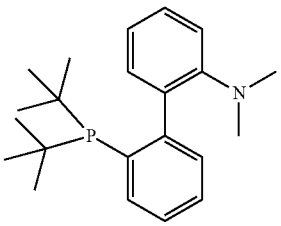

F

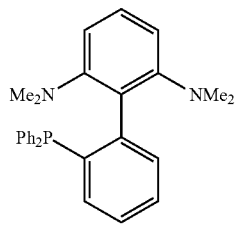

G

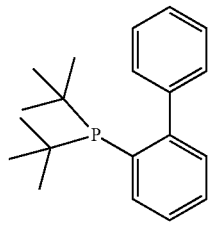

H

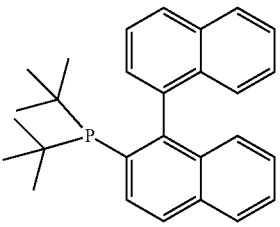

I

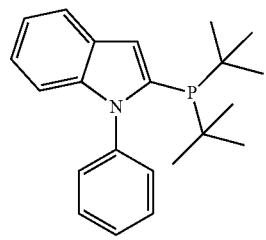

J

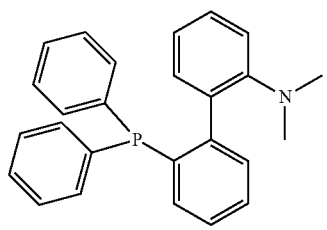

-continued

K
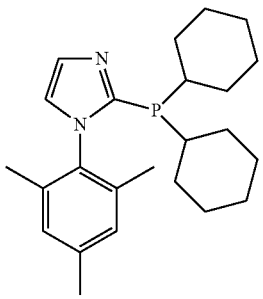

L
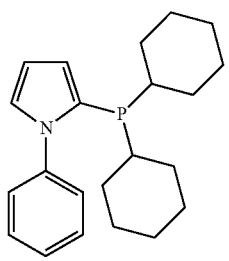

M
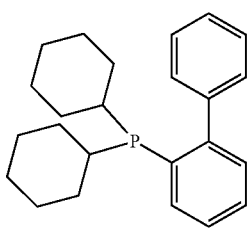

N
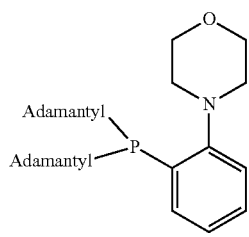

O
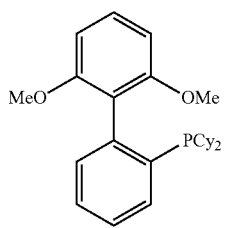

P
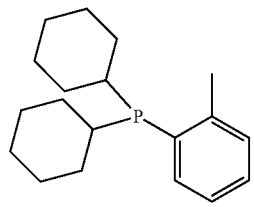

In one embodiment of the present invention, the inventive process is characterized in that the transition metal catalyst TMC1 is selected from a compound of the following formulas.

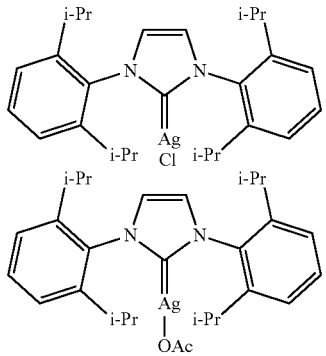

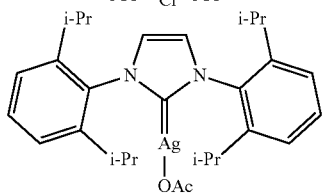

The molar ratio of the bulky ligand to the transition metal of transition metal catalyst TMC1 can be varied in wide range. Preferably the molar ratio of the bulky ligand to the transition metal is below 2. More preferably the ratio of the bulky ligand to the transition metal is in the range from 0.2 to 1.8, even more preferably in the range from 0.3 to 1.5, in particular in the range from 0.4 to 1.2.

In one embodiment of the present invention, the inventive process is characterized in that the molar ratio of the bulky ligand to the transition metal of transition metal catalyst TMC1 is in the range from 0.4 to 1.2.

In the inventive process the amount of transition metal catalyst TMC1 used in process step a) based on the amount of propargylic alcohol of formula II can be varied in a wide range. Usually the transition metal catalyst TMC1 is used in a sub-stoichiometric amount relative to the propargylic alcohol of formula II. Typically, the amount of transition metal catalyst TMC1 is not more than 50 mol %, frequently not more than 20 mol % and in particular not more than 10 mol % or not more than 5 mol %, based on the amount of propargylic alcohol of formula II. An amount of transition metal catalyst TMC1 of from 0.001 to 50 mol %, frequently from 0.001 mol % to 20 mol % and in particular from 0.005 to 5 mol %, based on the amount the propargylic alcohol of formula II is preferably used in the process of the invention. Preference is given to using an amount of transition metal catalyst TMC1 of from 0.01 to 5 mol %. All amounts of transition metal complex catalyst indicated are calculated as transition metal and based on the amount of propargylic alcohol.

In one embodiment of the present invention, the inventive process is characterized in that the amount of transition metal catalyst TMC1 used in process step a) based on the amount of propargylic alcohol of formula II is in the range from 0.005 to 5 mol %.

The reaction can principally be performed according to all processes known to a person skilled in the art which are suitable for the reaction of primary propargylic alcohols with $CO_2$.

The $CO_2$ used for the carboxylation-cyclisation reaction can be used in pure form or, if desired, also in the form of mixtures with other, preferably inert gases, such as nitrogen or argon. Preference is given to using $CO_2$ in undiluted form.

The reaction is typically carried at a $CO_2$ pressure in the range from 0.1 to 200 bar, preferably in the range from 1 to 50 bar, more preferably in the range from 1 to 40 bar.

In one embodiment of the present invention, the inventive process is characterized in that the process step a) is performed at a pressure in the range from 1 to 50 bar, more preferably in the range from 1 to 40 bar.

The reaction can principally be performed continuously, semi-continuously or discontinuously. Preference is given to a continuous process.

The reaction can principally be performed in all reactors known by a person in the art for this type of reaction and therefore, will select the reactors accordingly. Suitable reactors are described and reviewed in the relevant prior art, e.g. appropriate monographs and reference works such as mentioned in U.S. Pat. No. 6,639,114 B2, column 16, line 45-49. Preferably, for the reaction an autoclave is employed which may have an internal stirrer and an internal lining.

The composition obtained in the carboxylation-cyclisation reaction of the present invention comprises an unsubstituted Exo-Vinylene carbonate, that is a cyclic carbonate of formula Ia or Ib.

Process step a) of the inventive process can be performed in a wide temperature range. Preferably process step a) is performed at a temperature in the range preferably in the range from 0° C. to 150° C. and particularly preferably in the range from 10° C. to 80° C. Temperatures below 100° C. have surprisingly been found to be particularly advantageous.

In one embodiment of the present invention, the inventive process is characterized in that the process step a) is performed at a temperature in the range from 0° C. to 100° C., preferably in the range from 10° C. to 80° C.

The process of the invention can be carried out in the presence of a solvent. Suitable solvents are selected from aliphatic hydrocarbons, aromatic hydrocarbons, halogenated hydrocarbons, amides, ureas, nitriles, sulfoxides, sulfones, esters, carbonates, ethers, alcohols and mixtures thereof. Preferred solvents are
- aliphatic hydrocarbons such as pentane, hexane, heptane, octane or cyclohexane;
- aromatic hydrocarbons such as benzene, toluene, xylenes, ethylbenzene, mesitylene or benzotrifluoride;
- halogenated hydrocarbons such as dichloromethane,
- amides such as dimethylformamide, diethylformamide, N-methylpyrrolidone, N-ethylpyrrolidone or dimethylacetamide;
- ureas such as tetramethylurea, N,N-dimethylimidazolinone (DMI) and N,N-dimethylpropyleneurea (DMPU);
- nitriles such as acetonitrile or propionitrile;
- sulfoxides such as dimethyl sulfoxide;
- sulfones such as sulfolane;
- esters such as methyl acetate, ethyl acetate, t-butyl acetate;
- carbonates such as diethyl carbonate, ethylene carbonate and propylene carbonate; and
- ethers such as dioxane, tetrahydrofuran, diethyl ether, dibutyl ether, methyl t-butyl ether, diisopropyl ether or diethylene glycol dimethyl ether;

If desired, mixtures of two or more of the afore-mentioned solvents can also be used.

Preference is given to using dichloromethane, acetone, dimethylformamide or acetonitrile as solvents.

In one embodiment of the present invention, the inventive process is characterized in that the reaction is carried out in the presence of a solvent selected from aliphatic hydrocarbons, aromatic hydrocarbons, halogenated hydrocarbons, amides, ureas, nitriles, sulfoxides, sulfones, esters, carbonates, ethers, alcohols and mixtures thereof, preferably selected from dichloromethane, acetone, dimethylformamide or acetonitrile.

Alternatively, the process of the invention can be carried out in the absence of any of the above-mentioned organic solvent, so-called neat conditions, preferably in the presence of liquid or supercritical carbon dioxide, in particular in the presence of supercritical carbon dioxide.

Alternatively, the process of the invention can be carried out in the presence of liquid or supercritical carbon dioxide, in particular in the presence of supercritical carbon dioxide, which is mixed with one of the above-mentioned organic solvent, so-called $CO_2$-expanded solvents.

The composition obtained in the carboxylation-cyclisation of the invention comprises an unsubstituted Exo-Vinylene carbonate, the cyclic carbonate of formula Ia or Ib.

The work-up of the reaction mixture of the inventive process and the isolation of the cyclic carbonate of formula Ia or Ib are effected in a customary manner, for example by filtration, an aqueous extractive work-up or by a distillation, for example under reduced pressure. The cyclic carbonate of formula Ia or Ib may be obtained in sufficient purity by applying such measures or a combination thereof, obviating additional purification steps. Alternatively, further purification can be accomplished by methods commonly used in the art, such as chromatography.

In one embodiment of the present invention, the inventive process is characterized in that the cyclic carbonates of formula Ia or Ib or mixtures thereof are separated from the transition metal catalyst TMC1 after process step a) via distillation.

The distillation residue usually still comprises the transition metal catalyst TMC1 in an active form, that can be reused in a new carboxylation-cyclisation reaction step, that is a new process step a. As long as the distillation conditions, in particular the temperature treatment, are not too harsh, the transition metal catalyst TMC1 remains active.

In one embodiment of the present invention, the inventive process is characterized in that the transition metal catalyst TMC1 is recycled to the reaction step a) after the cyclic carbonate of formula Ia or Ib or mixture thereof were removed via distillation.

The cyclic carbonates of formula Ia or Ib or mixtures thereof, which are prepared according to the inventive process show a high purity and are advantageously used in applications such as reactive diluent in the manufacture of epoxy resins, as electrolyte additive in electrochemical storage systems or as monomer in polymerization reactions A further aspect of the invention is the use of the cyclic carbonates of formula Ia or Ib or mixtures thereof prepared according to the above described inventive process as reactive diluent in the manufacture of epoxy resins, as electrolyte additive in electrochemical storage systems or as monomer in polymerization reactions.

The inventive process for preparing cyclic carbonates of formula Ia or Ib or mixtures thereof as described above allows not only the preparation of known compounds (e.g. $R^1$=H) but also the preparation of new compounds, which can be used as reactive diluent in the manufacture of epoxy resins, as electrolyte additive in electrochemical storage systems, as monomer in polymerization reactions or as building blocks in the synthesis of active compounds for pharmaceutical or agricultural applications.

A further aspect of the invention is a cyclic carbonate of formula Ia' or Ib',

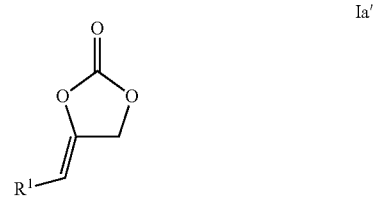

Ia'

-continued

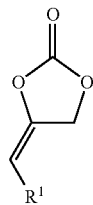

Ib' wherein $R^1$ is —$CH_2OR^{13}$, wherein $R^{13}$ is hydrogen, $SiH_3$ or an organic radical with 1 to 40 carbon atoms, preferably hydrogen, $SiR^{14a}R^{14b}R^{14c}$, $C(O)R^{15}$ or $C(O)OR^{16}$, more preferably hydrogen, $C(O)R^{15}$ or $C(O)OR^{16}$ wherein $R^{14a}R^{14b}R^{14c}$ are identical or different, and are each independently from each other hydrogen or an organic radical with 1 to 40 carbon atoms, preferably $C_1$-$C_6$ alkyl or $C_6$ to $C_{14}$ aryl, more preferably methyl, ethyl, i-propyl, tert.-butyl or phenyl, $R^{15}$ is hydrogen or an organic radical with 1 to 40 carbon atoms, preferably hydrogen, $C_1$-$C_6$ alkyl or $C_6$ to $C_{14}$ aryl, more preferably hydrogen, methyl, ethyl,-propyl or phenyl and $R^{16}$ is an organic radical with 1 to 40 carbon atoms, preferably $C_1$-$C_6$ alkyl or $C_6$ to $C_{14}$ aryl, more preferably methyl, ethyl,-propyl or phenyl.

The inventive cyclic carbonates of formula Ia' or Ib' are derivatives of (E or Z)-4-(2-hydroxyethylidene)-1,3-dioxolan-2-one, wherein the hydroxy group is preferably protected as corresponding ester or carbonate, or (E or Z)-4-(2-hydroxyethylidene)-1,3-dioxolan-2-one itself.

Preferred examples of the inventive cyclic carbonates of formula Ia' or Ib' are:

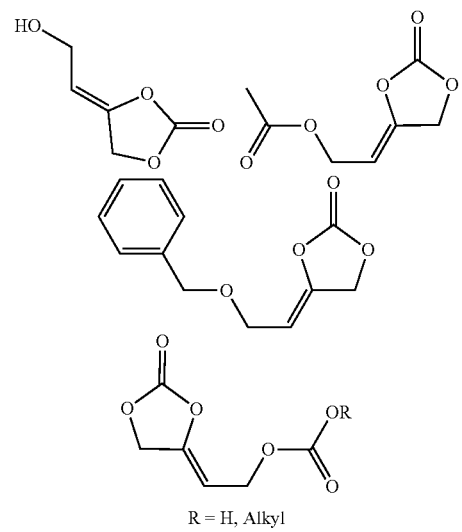

R = H, Alkyl

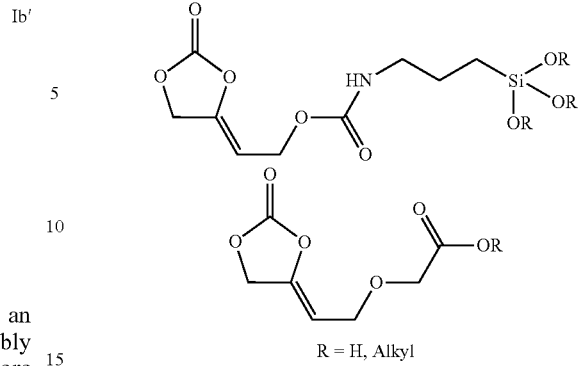

R = H, Alkyl

Preferred examples of cyclic carbonate of formula Ia' or Ib' are those, wherein $R^1$ is hydrogen, $C(O)R^{15}$ or $C(O)OR^{16}$, and wherein $R^{15}$ is hydrogen or methyl and $R^{16}$ is methyl.

The invention is illustrated by the examples which follow, but these do not restrict the invention.

Figures in percent are each based on % by weight, unless explicitly stated otherwise.

General

All chemicals and solvents were purchased from Sigma-Aldrich or ABCR and used without further purification.

$^1$H and $^{13}$C NMR spectra were recorded on Bruker Avance 200 MHz spectrometer and were referenced to the residual proton ($^1$H) or carbon ($^{13}$C) resonance peaks of the solvent. Chemical shifts (δ) are reported in ppm.

Used abbreviations: Davephos-Ligand A=2-Dicyclohexylphosphino-2'-(N,N-dimethylamino)biphenyl=L1; DCM=Dichloromethane; DIPEA=N,N-Diisopropylethylamine; DMAP=4-Dimethylaminopyridine; DMF=Dimethylformamide; PE=Petroleum ether; THF=Tetrahydrofuran; TMEDA=Tetramethylethylenediamine;

Ligands

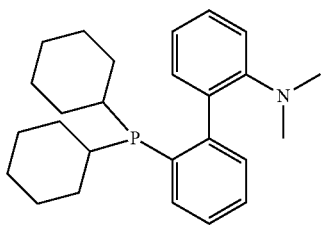

L1

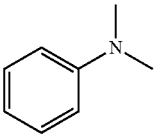

C-L2

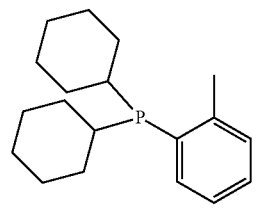

L3

| | |
|---|---|
| L4 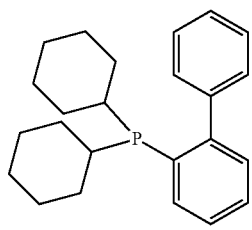 | L10 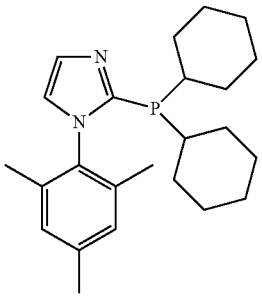 |
| L5 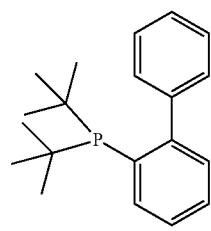 | L11 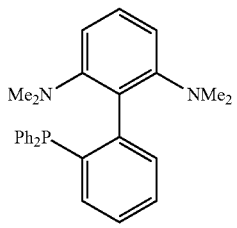 |
| L6 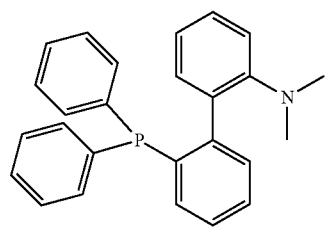 | L12 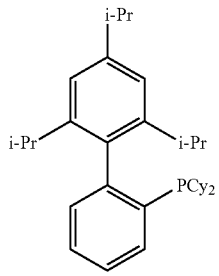 |
| L7 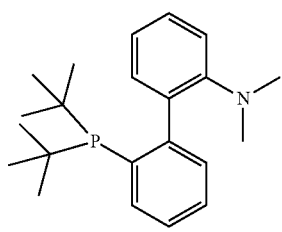 | L13 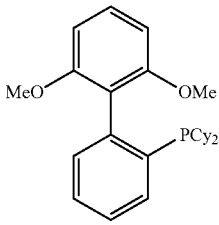 |
| L8 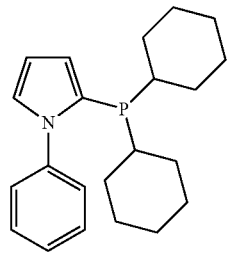 | L14 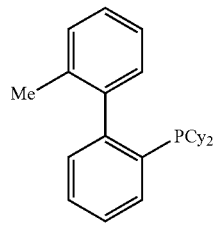 |
| L9 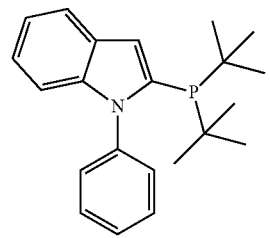 | L15 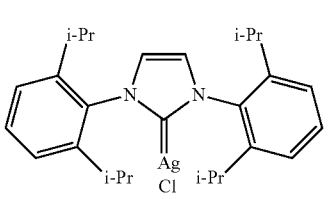 |

-continued

L16
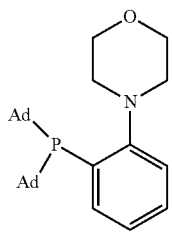

L17
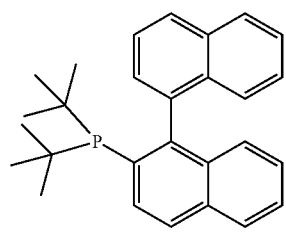

L18
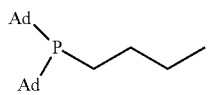

L19
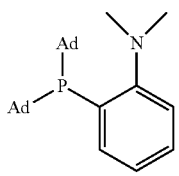

Protocols for Carboxylation Reactions

Standard Procedure A

Screening reactions were performed in a ChemSpeed Accelerator SLT 106 high-throughput robot system. Alcohol 1 (1 mmol), [M]-catalyst (0.05 mmol) and ligand (0.05 mmol) in organic solvent (2 mL) were pressurized with $CO_2$ (20 bar) and stirred at room temperature for 12 h. After releasing the $CO_2$ overpressure, anisole (1 mmol) and $CDCl_3$ (1 mL) were added to the reaction mixture and stirred for 5 min. The resulting mixture was analyzed by $^1H$ NMR to determine the yield.

Standard Procedure B

A Fisher-Porter tube with Teflon-coated stirrer-bar was charged with the alcohol (5 mmol), [M]-catalyst (0.25 mmol), and ligand (0.25 mmol) and solvent (5 mL). The reaction mixture was pressurized with $CO_2$ (8 bar) and stirred at room temperature for 16 h. Then $CO_2$ overpressure was carefully released and solvent evaporated. The resulting crude mixture was distilled by a Kugelrohr (0.5 mbar, 100° C.). The corresponding cyclic carbonate product was obtained pure.

1. Ligand Variation

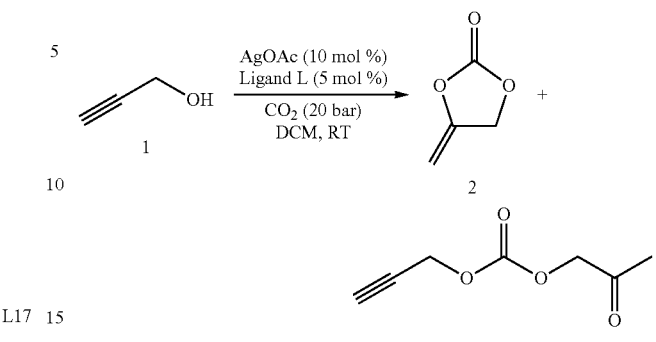

Table 1 summarizes the results of experiments, which were run in analogy to standard procedure A using a metal-ligand ratio of 2 to 1.

TABLE 1

| Entry | Ligand L [5 mol %] | Yield of 1 [%] | 2 [%] | 3 [%] |
|---|---|---|---|---|
| 1 | L1 | 0 | 99 | 0 |
| 2 | C-L2 | 83 | 0 | 0 |
| 3 | L3 | 0 | 21 | 35 |
| 4 | L4 | 0 | 41 | 15 |
| 5 | L5 | 0 | 60 | 20 |
| 6 | L6 | 0 | 51 | 27 |
| 7 | L7 | 0 | 74 | 7 |
| 8 | L8 | 0 | 43 | 35 |
| 9 | L9 | 0 | 54 | 15 |
| 10 | L10 | 0 | 47 | 20 |
| 11 | L11 | 0 | 62 | 18 |
| 12 | L12 | 0 | 82 | 5 |
| 13 | L13 | 0 | 32 | 4 |
| 14 | L14 | 0 | 94 | 7 |
| 15 | L15 | 80 | 10 | 10 |
| 16 | L16 | 0 | 41 | 55 |
| 17 | L17 | 0 | 57 | 0 |
| 18 | L18 | 80 | 2 | 0 |
| 19 | L19 | 0 | 90 | 0 |

2. Ligand Variation and Variation of Catalyst Composition

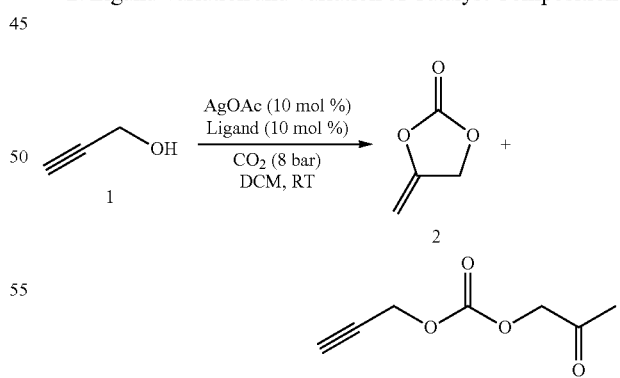

Table 2 summarizes the results of inventive and comparative experiments, which were run in analogy to standard procedure B using different amounts of metal and ligand. Propargyl alcohol 1 (5 mmol), AgOAc (0.5 mmol) and ligand L (0.5 mmol) in anhydrous DCM (2 mL) were pressurized with $CO_2$ (8 bar) and stirred for 16 h. Yields were determined by $^1$H NMR spectroscopy using anisole as an internal standard. Isolated yields are given in parentheses.

TABLE 2

| Entry | AgOAc [mol %] | Ligand L [10 mol %] | Yield of 2 [%] |
|---|---|---|---|
| 1 | 10 | (n-$C_7H_{15}$)$_4$NBr | — |
| 2 | 10 | $Et_3N$ | — |
| 3 | 10 | DBU | — |
| 4 | 10 | TMEDA | — |
| 5 | 10 | $Cs_2CO_3$ | — |
| 6 | 10 | L4 | 60 |
| 7 | 10 | L1 | 75 |
| 8 | 10 | L1 (5 mol %) | 85 |
| 9 | 10 | L1 | 83 |
| 10 | 5 | L1 (5 mol %) | 91 (86) |

3. Variation of the Transition Metal Compound (Pre-Catalyst) and Ligand

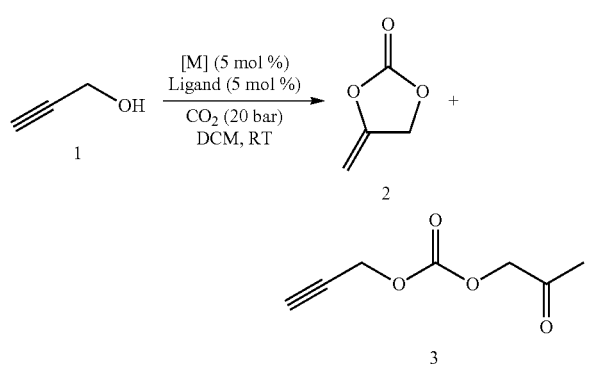

Table 3 summarizes the results of inventive and comparative experiments, which were run in analogy to standard procedure A. Propargyl alcohol 1 (1 mmol), transition metal compound [M] (0.05 mmol) and ligand L (0.05 mmol) in anhydrous DCM (2 mL) were pressurized with $CO_2$ (20 bar) and stirred for 12 h. Yields were determined by $^1$H NMR spectroscopy using anisole as an internal standard.

TABLE 3

| Entry | [M] [5 mol %] | Ligand L [5 mol %] | Yield of 2 [%] |
|---|---|---|---|
| 1 | AgOAc | L1 | 98 |
| 2 | AgF | L1 | 98 |
| 3 | $AgNO_3$ | L1 | 20 |
| 4 | AgTFA | L1 | 18 |
| 5 | $Ag_2CO_3$ | L1 | 72 |
| 6 | NaOAc | L1 | 0 |
| 7 | CuOAc | L1 | traces |
| 8 | CuOAc | DMAP | 0 |
| 9 | CuOAc | 1,10-phenanthroline | 0 |
| 10 | CuOAc | 2,2'-bipyridine | 0 |
| 11 | CuOAc | DBU | 0 |
| 12 | CuOAc | $NEt_3$ | 0 |
| 13[a] | IPrAgOAc | — | 99 |

[a]0.035 mmol propargylic alcohol, 1 mol % IPrAgOAc, 0.7 mL $CD_3CN$, 20 bar $CO_2$; IPrAgOAc was prepared according to a literature procedure: D. V. Partyka, T. J. Robilotto, J. B. Updegraff III, M. Zeller, A. D. Hunter, T. G. Gray, *Organometallics* 2009, 28, 795-801.

TABLE 3-continued

| Entry | [M] [5 mol %] | Ligand L [5 mol %] | Yield of 2 [%] |
|---|---|---|---|

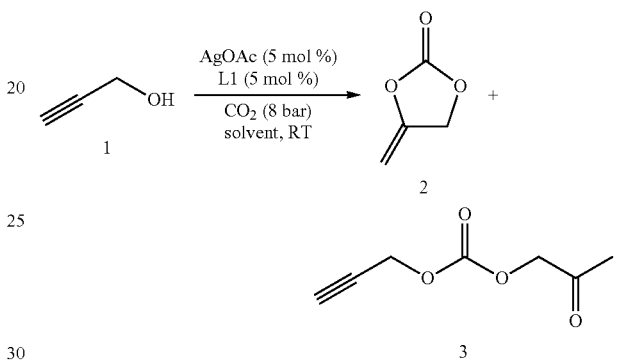

4. Variation of the Solvent

Table 4 summarizes the results of inventive experiments, which were run in analogy to standard procedure B. Propargyl alcohol 1 (5 mmol), AgOAc (0.25 mmol) and L1 (0.25 mmol) in solvent (5 mL) were pressurized with $CO_2$ (8 bar) and stirred for 16 h. Yields were determined by $^1$H NMR spectroscopy using anisole as an internal standard.

TABLE 4

| Entry | solvent | Yield of 2 [%] |
|---|---|---|
| 1 | DCM | 98 |
| 2 | acetone | 96 |
| 3 | DMF | 84 |
| 4 | MeCN | 85 |

5. Recycling of the Catalytic System

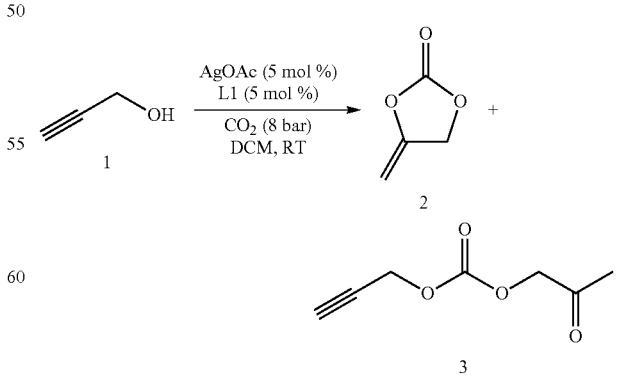

Table 5 summarizes the results of inventive experiments, wherein the catalyst system was recycled and which were run in analogy to standard procedure B. Propargyl alcohol 1 (5 mmol), AgOAc (0.25 mmol) and L1 (0.25 mmol) in solvent (5 mL) were pressurized with $CO_2$ (8 bar) and stirred for 16 h. Yields were determined by $^1H$ NMR spectroscopy using anisole as an internal standard. After a Kugelrohrdestillation (100° C., 0.5 mbar) product was isolated and the residual crude used for further reaction.

TABLE 5

| Cycle (Recycling the catalyst system) | Yield 2 [%] |
|---|---|
| 1 | 98 |
| 2 | 84 |
| 3 | 70 |
| 4 | 70 |

6. Variation of the Propargylic Alcohol of Formula II

6.1 Use of 1,4-Butynediol as Propargylic Alcohol of Formula II

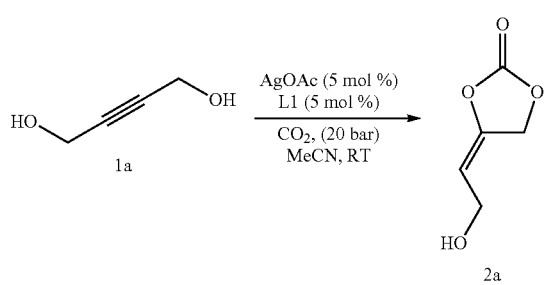 [SMILES: OCC#CCO ; O=C1OC/C(=C\CO)O1]

In a ChemSpeed Accelerator SLT 106 high-throughput robot system, 1,4-Butynediol (1 mmol), AgOAc (0.05 mmol) and L1 (0.05 mmol) in MeCN (2 mL) were pressurized with $CO_2$ (20 bar) and stirred at room temperature for 12 h. After releasing the $CO_2$ overpressure, anisole (1 mmol) and $CDCl_3$ (1 mL) were added to the reaction mixture and stirred for 5 min. The resulting mixture was analyzed by $^1H$ NMR to determine the yield. Isolation was done by column chromatography (silica, EtOAc/hexane gradient).

(E)-4-(2-hydroxyethylidene)-1,3-dioxolan-2-one 2a $^1H$ NMR (400 MHz, $CDCl_3$) δ 5.01-4.98 (m, 3H), 4.24-4.21 (m, 2H), 2.9 (s, 1H).
$^{13}C$ NMR (50 MHz, $CDCl_3$) δ 152.6, 143.1, 102.4, 67.4, 55.8.
(Z)-4-(2-hydroxyethylidene)-1,3-dioxolan-2-one

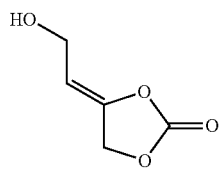

Colorless oil, 423 mg (65%). $R_f$(EtOAc/PE 1:1)=0.62. $^1H$ NMR (200 MHz, $CDCl_3$): δ=4.97-4.88 (m, 3H), 4.18-4.15 (m, 2H), 3.33 (s, 1H). $^{13}C$ NMR (50 MHz, $CDCl_3$): δ=152.9, 143.2, 102.4, 67.6, 55.7. IR (KBr): ν=3649, 3565, 3134, 3026, 2974, 2416, 2261, 1856 (C=O), 1812, 1694. 1465, 1395. 1359, 1287, 1129, 1062, 974, 853, 767, 727, 548 $cm^{-1}$.
HRMS (EI): m/z calcd. for $C_5H_6O_4$: 130.0260 [M$^+$]; found: 130.0259.

6.2 Use of 4-hydroxybut-2-yn-1-yl acetate as Propargylic Alcohol of Formula II

6.2.1 Synthesis of 4-hydroxybut-2-yn-1-yl acetate

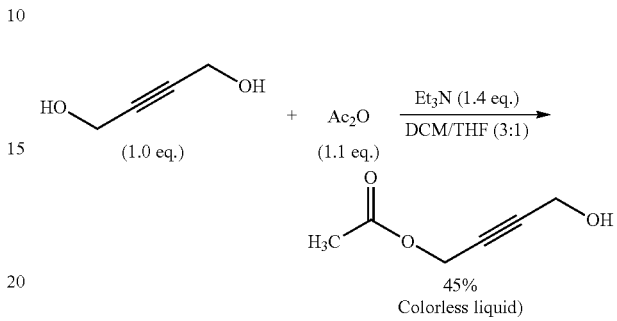

Distilled $Et_3N$ (10.2 mL, 81.2 mmol, 1.4 eq.) was added to a solution of but-2-yne-1,4-diol (5.0 g, 58.0 mmol, 1.0 eq.) in dry DCM/THF (24 mL/8 mL), and the resulting suspension was stirred at room temperature until dissolution was complete. Acetic anhydride (6.0 mL, 63.5 mmol, 1.1 eq.) was then added to the reaction mixture at 0° C. dropwise over 30 min. The reaction mixture was then warmed to room temperature and stirred overnight. Water was added and the reaction mixture was extracted with DCM (3044×4 mL). The collected organic layers were dried and the solvents were evaporated in vacuo. Flash chromatography of the crude products (silica gel, EtOAc/PE 2:3) gave the pure product as a colourless oil (3.34 g, 45%).
$^1H$ NMR (400 MHz, $CDCl_3$): δ=4.64-4.63 (m, 2H), 4.22-4.21 (m, 2H), 3.17 (br.s, 1H), 2.03 (s, 3H). $^{13}C$ NMR (101 MHz, $CDCl_3$): δ=170.7, 85.2, 79.2, 52.4, 50.5, 20.7. HRMS (ESI, 70 eV): m/z calcd. for $C_6H_8O_3$: 128.0468 [M$^+$]; found: 128.0461.

6.2.2 Synthesis of (E)-2-(2-oxo-1,3-dioxolan-4-ylidene)ethyl acetate 2b

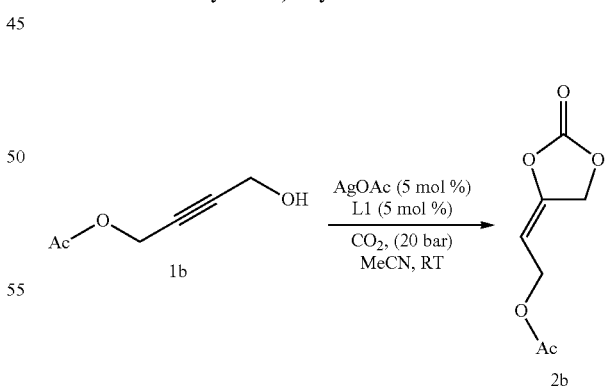

In a ChemSpeed Accelerator SLT 106 high-throughput robot system. 4-hydroxybut-2-yn-1-yl acetate (1b, 1 mmol), AgOAc (0.05 mmol) and L1 (0.05 mmol) in MeCN (2 mL) were pressurized with $CO_2$ (20 bar) and stirred at room temperature for 12 h. After releasing the $CO_2$ overpressure, anisole (1 mmol) and $CDCl_3$ (1 mL) were added to the reaction mixture and stirred for 5 min. The resulting mixture was analyzed by $^1$H NMR to determine the yield. Isolation was done by column chromatography (silica, EtOAc/hexane gradient).

(E)-2-(2-oxo-1,3-dioxolan-4-ylidene)ethyl acetate 2b $^1$H NMR (400 MHz, CDCl$_3$) δ 4.97-4.96 (m, 2H), 4.92-4.88 (m, 1H), 4.64-4.59 (m, 2H), 2.9 (s, 3H).
$^{13}$C NMR (50 MHz, CDCl$_3$) δ 170.5, 151.9, 145.2, 97.4, 67.3, 57.4, 20.5.

6.2.3 (Z)-2-(2-oxo-1,3-dioxolan-4-ylidene)ethyl acetate

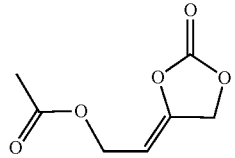

Colorless oil, 688 mg (80%). R$_f$(EtOAc/PE 3:7)=0.35. $^1$H NMR (400 MHz, CDCl$_3$): δ=5.01-4.92 (m, 3H), 4.71-4.67 (m, 2H), 2.05 (m, 3H). $^{13}$C NMR (101 MHz, CDCl$_3$): δ=170.8, 152.0, 145.4, 97.9, 67.4, 57.7, 20.9. IR (KBr): ν=2971, 2257, 1830 (C=O), 1727 (C=O), 1462, 1374, 1435, 1132, 1231, 1096, 1028, 965, 765. 733 cm$^{-1}$. HRMS (EI): m/z calcd. for C$_7$H$_8$O$_5$: 172.0366 [M$^+$]; found: 172.0391. Anal. Calcd. for C$_7$H$_8$O$_4$: C, 48.84%, H, 4.68%, Found: C, 49.23%, H, 5.00%.

6.3 Synthesis of Different Alcohols of Formula II

6.3.1 Synthesis of 4-(benzyloxy)but-2-yn-1-ol

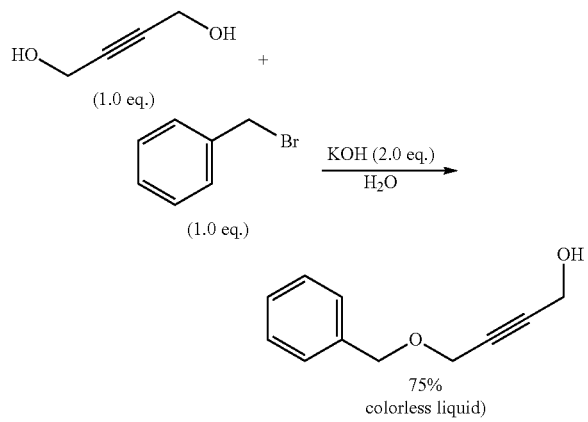

But-2-yne-1,4-diol (3.9 g, 45.2 mmol, 2.0 eq.) was added into a solution of KOH (2.5 g, 44.5 mmol, 2.0 eq.) in water (40 mL). The mixture was stirred for 10 min at room temperature. Benzyl bromide (3.9 g, 22.8 mmol, 1.0 eq.) was then added into the above solution dropwise and the mixture was stirred for 2 days at room temperature. The reaction mixture was extracted with DCM, the combined organic phases were washed with brine and dried over MgSO$_4$. The organic layer was concentrated in vacuo. Flash chromatography on silica gel (EtOAc/PE 2:3) yielded the desired mono-benzylated alcohol as colourless oil (3.0 g, 75%).

$^1$H NMR (400 MHz, CDCl$_3$): δ=7.25-7.15 (m, 5H), 4.48 (s, 2H), 4.16-4.17 (m, 2H), 4.10-4.09 (m, 2H), 2.81 (s, 1H). $^{13}$C NMR (101 MHz, CDCl$_3$): δ=137.2, 128.4 (2C), 128.1, 127.9 (2C), 85.1, 81.3, 71.7, 57.4, 50.7. HRMS (ESI, 70 eV): m/z calcd. for C$_{11}$H$_{12}$O$_2$: 176.0832 [M$^+$]; found: 176.0827.

6.3.2 Synthesis of 4-hydroxybut-2-yn-1-yl methyl carbonate

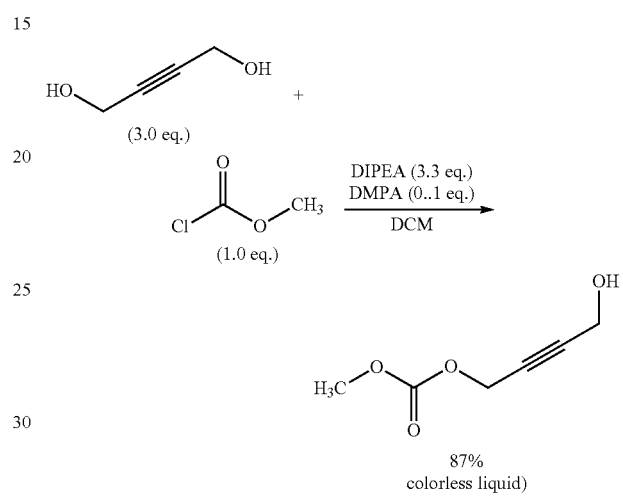

But-2-yne-1,4-diol (15 g, 174 mmol, 3 eq.) dissolved in anhydrous DCM (350 mL) was cooled to 0° C. DIPEA (33.5 mL, 181.7 mmol, 3.3 eq.) and DMAP (708 mg, 5.8 mmol, 0.1 eq.) were then added to the above solution followed by the dropwise addition of methyl chloroformate (4.49 mL, 58.1 mmol, 1.0 eq.) via a syringe. The reaction mixture was stirred at 0° C. for 2 h followed by stirring it overnight at room temperature. The reaction mixture was concentrated to half of its original volume followed by the addition of Et$_2$O and NaHCO$_3$. The phases were separated and the organic phase was washed three times with sat. NaHCO$_3$ before drying it over MgSO$_4$. The solvent was removed under reduced pressure and the crude was purified by column chromatography (silica gel, EtOAc/PE 3:7) yielding the product as a colourless oil (7.3 g, 87%).

$^1$H NMR (400 MHz, CDCl$_3$): δ=4.77-4.76 (m, 2H), 4.30-4.29 (m, 2H), 3.81 (s, 3H). $^{13}$C NMR (101 MHz, CDCl$_3$): δ=155.3, 85.9, 79.1, 55.6, 55.2, 50.9.

6.4 Synthesis of Different 1,3-dioxolan-2-ones

General Procedure for the carboxylative Cyclization of but-2-ynol Derivatives

A steel autoclave was charged with Alkynol (5.0 mmol), AgOAc (1 or 2 mol %), Davephos-Ligand (1 or 2 mol %) and solvent (10 mL) under atmospheric conditions. The reaction mixture was pressurized with CO$_2$ (20 bar) and stirred at room temperature for 18 h. Then CO$_2$ overpressure was carefully released and solvent evaporated. The resulting crude mixture was purified by flash column chromatograph

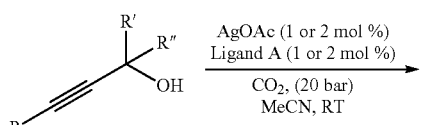
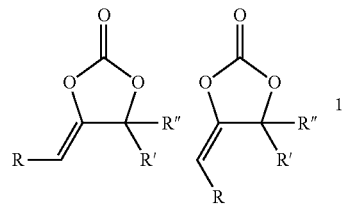

6.4.1 Characterization of the Isolated exo-vinylene carbonate Products

6.4.1.1 4-methylene-1,3-dioxolan-2-one

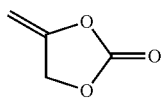

White solid, 450 mg (90%), mp: 28.3-29.0° C. $R_f$(EtOAc/PE 3:7)=0.38. $^1$H NMR (200 MHz, CDCl$_3$): δ=4.98-4.96 (m, 2H), 4.84-4.80 (m, 1H), 4.42-4.37 (m, 1H). $^{13}$C NMR (50 MHz, CDCl$_3$): δ=152.8, 148.8, 87.1, 67.6. IR (KBr): ν=2974, 1836 (C=O), 1695, 1394, 1464, 1359, 1287, 1128, 1062, 974, 853, 767, 727 cm$^{-1}$. HRMS (EI): m/z calcd. for C$_4$H$_4$O$_3$: 100.0155 [M$^+$]; found: 100.1054.

6.4.1.2 (Z)-5-(2-hydroxy-2-methylpropylidene)-4,4-dimethyl-1,3-dioxolan-2-one (Comparison)

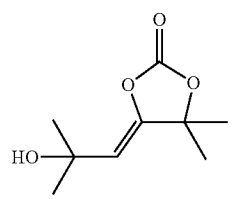

Colorless oil, 837 mg (90%). $R_f$(EtOAc/PE 3:7)=0.26. $^1$H NMR (200 MHz, CDCl$_3$): δ=4.70 (s, 1H), 2.91 (s, 1H), 1.42 (s, 6H), 1.27 (s, 6H). $^{13}$C NMR (50 MHz, CDCl$_3$): δ=151.1, 149.0, 109.6, 84.9, 69.4, 29.8 (2C), 27.4 (2C). IR (KBr): ν=3461, 2982, 2937, 1818 (C=O), 1712, 1548, 1563, 1373, 1286, 1250, 1168, 1055, 1023, 980, 924, 770 cm$^{-1}$. HRMS (ESI): m/z calcd. for C$_9$H$_{14}$O$_4$: 187.0965 [M+H$^{30}$]; found: 187.0968.

6.4.1.3 4-methyl-5-methylene-1,3-dioxolan-2-one (Comparison)

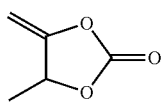

Light yellow oil, 524 mg (92%). $R_f$(EtOAc/PE 3:7)=0.57. $^1$H NMR (200 MHz, CDCl$_3$): δ=5.31-5.20 (m, 1H), 4.82 (dd, J=4.0 Hz, 2.5 Hz, 1H), 4.35 (dd, J=4.0 Hz, 2.0 Hz m, 1H), 1.56 (d, J=6.5 Hz, 3H). $^{13}$C NMR (50 MHz, CDCl$_3$): δ=154.7, 152.0, 86.7, 76.3, 20.5. IR (KBr): ν=2991, 1837 (C=O), 1752, 1686, 1458, 1379, 1351, 1324, 1156, 1112, 1080, 1044, 1007, 856, 769, 710, 640, 587, 556 cm$^{-1}$. HRMS (EI): m/z calcd. for C$_5$H$_6$O$_3$: 114.0311 [M$^+$]; found: 114.0326.

6.4.1.4 4,4-dimethyl-5-methylene-1,3-dioxolan-2-one (Comparison)

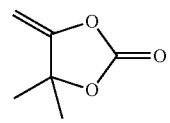

Viscous oil, 557 mg (87%). $R_f$(EtOAc/PE 3:7)=0.65. $^1$H NMR (200 MHz, CDCl$_3$): δ=4.74 (d, J=3.9 Hz, 1H), 4.31 (d, J=3.9 Hz, 1H) 1.58 (s, 6H). $^{13}$C NMR (50 MHz, CDCl$_3$): δ=158.8, 151.3, 85.4, 84.7, 27.6 (2C). HRMS (EI): m/z calcd. for C$_6$H$_8$O$_3$: 128.0468 [M$^+$]; found: 128.0469.

6.4.1.5 (Z)-methyl (2-(2-oxo-1,3-dioxolan-4-ylidene)ethyl) carbonate

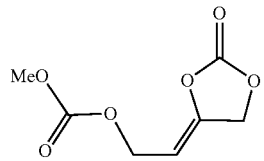 [SMILES: COC(=O)OC/C=C1/COC(=O)O1]

Colorless oil, 611 mg (65%). $R_f$(EtOAc/PE 3:7)=0.24. $^1$H NMR (400 MHz, CDCl$_3$): δ=5.02-4.97 (m, 3H), 4.81-4.77 (m, 2H), 3.80 (s, 3H). $^{13}$C NMR (101 MHz, CDCl$_3$): δ=155.8, 152.0, 146.1, 97.5, 67.5, 61.1, 55.3. IR (KBr): ν=3017, 2967, 2351, 2214, 1834 (C=O), 1749 (C=O), 1681, 1448, 1371, 1262, 1130, 1050, 943, 766, 567 cm$^{-1}$. HRMS (EI): m/z calcd. for C$_7$H$_8$O$_6$: 188.0315 [M$^+$]; found: 188.0303. Anal. Calcd. for C$_7$H$_8$O$_6$: C, 44.69, H, 4.29%, Found: C, 44.41%, H, 5.13%.

6.4.1.6 ((Z)-4-(2-(benzyloxy)ethylidene)-1,3-dioxolan-2-one

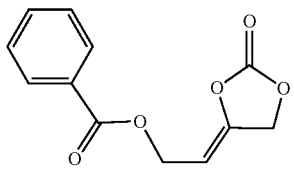 [SMILES: O=C1OC/C(=C/COC(=O)c2ccccc2)O1]

Colorless oil, 770 mg (70%). $R_f$(EtOAc/PE 3:7)=0.44. $^1$H NMR (400 MHz, CDCl$_3$): δ=7.37-7.29 (m, 5H), 4.99-4.92 (m, 3H), 4.53 (s, 2H) 4.23-4.18 (m, 2H). $^{13}$C NMR (101 MHz, CDCl$_3$): δ=152.4, 144.0, 137.9, 128.5 (2C), 127.9

(3C), 100.3, 72.8, 67.4, 63.4. IR (KBr): ν=3065, 3038, 3032, 2867, 1839 (C=O), 1723, 1455, 1381, 1274, 1210, 1108, 1045, 912, 734, 700 cm$^{-1}$. HRMS (EI): m/z calcd. for $C_{12}H_{12}O_4$: 220.0730 [M$^+$]; found: 220.0735. Anal. Calcd. for $C_{12}H_{12}O_4$: C, 65.45%, H, 5.49%, Found: C, 65.40%, H, 5.53%.

6.4.1.7 4-methyl-5-methylene-4-(4-methylpent-3-en-1-yl)-1,3-dioxolan-2-one (Comparison)

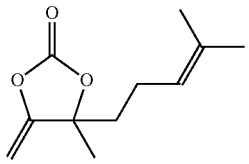

Colorless oil, 922 mg (94%). $R_f$(EtOAc/PE 3:7)=0.81. $^1$H NMR (300 MHz, CDCl$_3$): δ=5.07-5.01 (m, 1H), 4.80 (d, J=3.9 Hz, 1H), 4.27 (d, J=3.9 Hz, 1H), 2.15-1.97 (m, 2H) 1.94-1.84 (m, 1H), 1.76-1.68 (m, 1H), 1.66 (s, 3H), 1.57 (s, 6H). $^{13}$C NMR (75 MHz, CDCl$_3$): δ=157.7, 151.5, 133.3, 122.0, 87.2, 85.6, 40.3, 26.6, 25.7, 22.0, 17.7. IR (KBr): ν=2981, 1829 (C=O), 1685, 1451, 1379, 1303, 1260, 1221, 1183, 1154, 1121, 1102, 1069, 1033, 852, 767 cm$^{-1}$.

HRMS (EI): m/z calcd. for $C_{11}H_{16}O_3$: 196.1094 [M$^+$]; found: 196.1113. Anal. Calcd. for $C_{11}H_{16}O_3$: C, 67.32%, H, 8.22%, Found: C, 66.94%, H, 8.34%.

The invention claimed is:

1. A process for preparing a cyclic carbonate of formula Ia or Ib or a mixture thereof

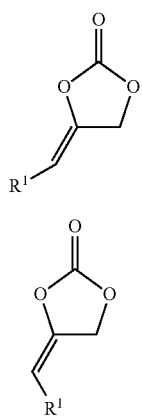

wherein R$^1$ is hydrogen or an organic radical having from 1 to 40 carbon atoms, the process comprising:
a) reacting a propargylic alcohol of formula II

wherein R$^1$ is defined as in formula Ia or Ib,
with carbon dioxide in the presence of at least one transition metal catalyst TMC1, which comprises: a transition metal selected from metals of groups 10, 11 and 12 of the periodic table of the elements; and at least one bulky ligand selected from the group of ligands consisting of a compound of formula III and a compound of formula IV

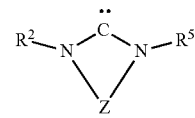

wherein D is P, As or Sb,
R$^2$, R$^3$, R$^4$ and R$^5$ are each independently an organic radical having from 1 to 40 carbon atoms,
and
Z is a divalent bridging group selected from —CR$^7$=CR$^8$—, —CR$^7$=N—, —CR$^7$R$^9$—CR$^8$R$^{10}$— and —CR$^7$R$^9$—CR$^8$R$^{10}$—CR$^{11}$R$^{12}$—, wherein R$^7$, R$^8$, R$^9$, R$^{10}$, R$^{11}$ and R$^{12}$ are each independently hydrogen or an organic radical having from 1 to 40 carbon atoms or two adjacent radicals R$^7$ and R$^8$ and/or R$^{10}$ and R$^{11}$ together with the atoms connecting them form a monocyclic or polycyclic, substituted or un-substituted, aliphatic or aromatic ring system which has from 4 to 40 carbon atoms and optionally comprises at least one heteroatom selected from the group of elements consisting of Si, Ge, N, P, O and S
thereby obtaining the cyclic carbonate of formula Ia or Ib or the mixture thereof in a yield of from 2% to 99%.

2. The process of claim 1, wherein R$^1$ is hydrogen, hydroxymethyl (—CH$_2$OH), acetoxy-methylene (—CH$_2$OC(O)CH$_3$), formyloxy-methylene (—CH$_2$OC(O)H) or —CH$_2$OC(O)OCH$_3$.

3. The process of claim 1, wherein the transition metal of the at least one transition metal catalyst TMC1 is Ag.

4. The process of claim 1, wherein the at least one transition metal catalyst TMC1 is prepared in situ by using a transition metal compound, which does not comprise any bulky ligand, and the compound of formula III or the compound of formula IV as a bulky ligand or a protonated form of the compound of formula IV represented by formula V,

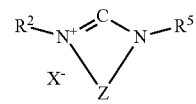

wherein R$^2$, R$^5$ and Z are defined as in formulae III or IV and X$^-$ is an anion equivalent, together with a base.

5. The process of claim 4, wherein the transition metal compound is selected from AgOAc, AgF, Ag$_2$O and Ag$_2$CO$_3$.

6. The process of claim 1, wherein the at least one bulky ligand is a compound of formula III.

7. The process of claim 1, wherein the at least one bulky ligand is selected from a compound of the following formulae A to P and mixtures thereof

| 31 | 32 |
|---|---|
| | -continued |
A
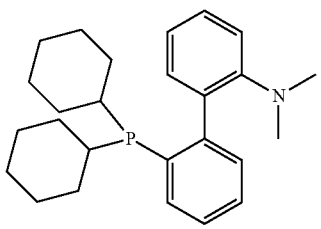
H
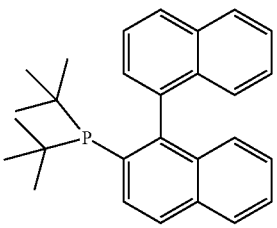
B
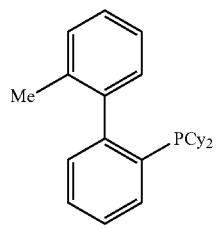
I
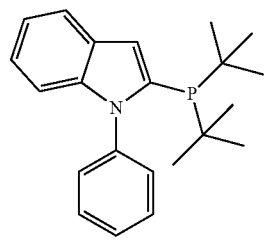
C
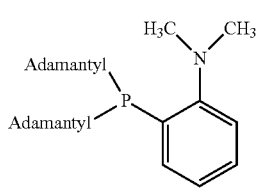
J
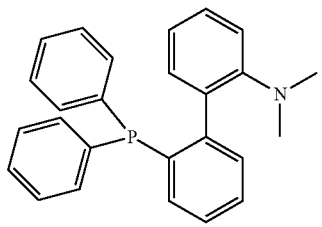
D
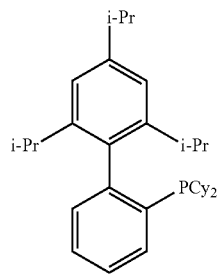
K
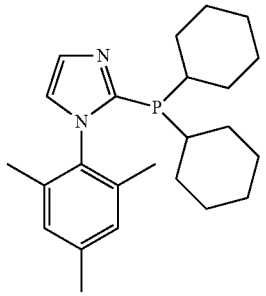
E
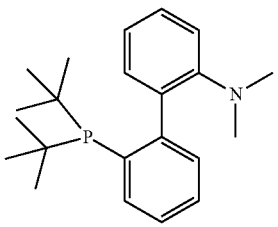
L
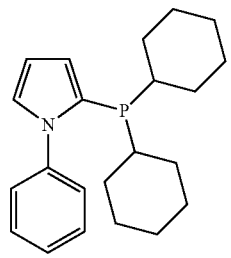
F
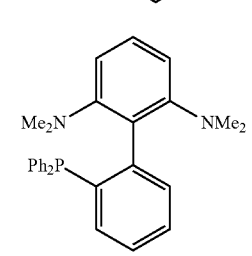
M
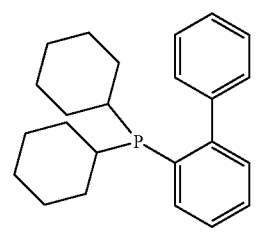
G
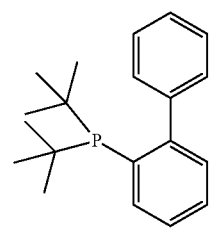

-continued

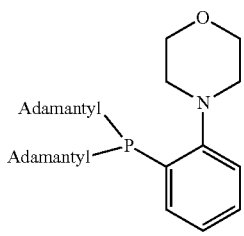
N

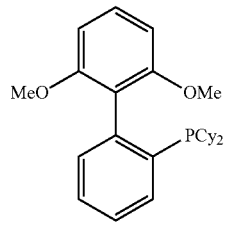
O

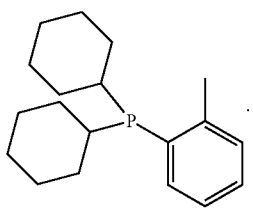
P

8. The process of claim 1, wherein a molar ratio of the at least one bulky ligand to the transition metal of the at least one transition metal catalyst TMC1 is in a range of from 0.4 to 1.2.

9. The process of claim 1, wherein an amount of the at least one transition metal catalyst TMC1 used in a) is in a range of from 0.005 to 5 mol %, based on an amount of the propargylic alcohol of formula II.

10. The process of claim 1, wherein a) is performed at a pressure in a range of from 1 to 50 bar.

11. The process of claim 1, wherein a) is performed at a temperature in a range of from 0° C. to 1° *C.

12. The process of claim 1, wherein a) is carried out in the presence of a solvent selected from the group consisting of aliphatic hydrocarbons, aromatic hydrocarbons, halogenated hydrocarbons, amides, ureas, nitriles, sulfoxides, sulfones, esters, carbonates, ethers, alcohols and mixtures thereof.

13. The process of claim 1, wherein the cyclic carbonate of formula Ia or Ib or the mixture thereof is separated from the at least one transition metal catalyst TMC1 after a) via distillation.

14. The process of claim 1, wherein the the at least one transition metal catalyst TMC1 is recycled to the reacting of a) after the cyclic carbonate of formula Ia or Ib or the mixture thereof is removed via distillation.

15. A process for preparing a cyclic carbonate of formula Ia or Ib or a mixture thereof

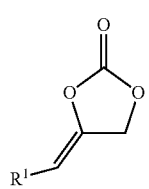
Ia

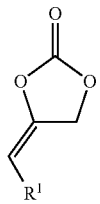
Ib wherein $R^1$ is hydrogen or an organic radical having from 1 to 40 carbon atoms, the process comprising:

a) reacting a propargylic alcohol of formula II

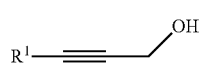
II wherein $R^1$ is defined as in formula Ia or Ib, with carbon dioxide in the presence of at least one transition metal catalyst TMC1, which comprises: a transition metal selected from metals of groups 10, 11 and 12 of the periodic table of the elements; and at least one bulky ligand selected from the group of ligands consisting of a compound of formula III and a compound of formula IV

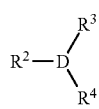
III

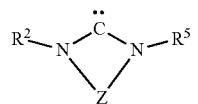
IV wherein D is P, As or Sb, $R^2$, $R^3$, $R^4$ and $R^5$ are each independently an organic radical having from 1 to 40 carbon atoms, and Z is a divalent bridging group selected from $-CR^7=CR^8-$, $-CR^7=N-$, $-CR^7R^9-CR^8R^{10}-$ and $-CR^7R^9-CR^8R^{10}-CR^{11}R^{12}-$, wherein $R^7$, $R^8$, $R^9$, $R^{10}$, $R^{11}$ and $R^{12}$ are each independently hydrogen or an organic radical having from 1 to 40 carbon atoms or two adjacent radicals $R^7$ and $R^8$ and/or $R^{10}$ and $R^{11}$ together with the atoms connecting them form a monocyclic or polycyclic, substituted or un-substituted, aliphatic or aromatic ring system which has from 4 to 40 carbon atoms and optionally comprises at least one heteroatom selected from the group of elements consisting of Si, Ge, N, P, O and S, wherein the at least one transition metal catalyst TMC1 is prepared in situ by using a transition metal compound, which does not comprise any bulky ligand, and the compound of formula III or the compound of formula IV as a bulky ligand or a protonated form of the compound of formula IV represented by formula V,

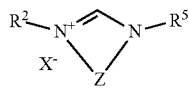

wherein $R^2$, $R^5$ and Z are defined as in formulae III or IV and $X^-$ is an anion equivalent, together with a base.

16. A process for preparing a cyclic carbonate of formula Ia or Ib or a mixture thereof

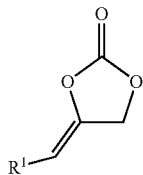

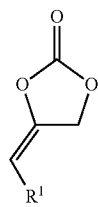

wherein $R^1$ is hydrogen or an organic radical having from 1 to 40 carbon atoms, the process comprising:

a) reacting a propargylic alcohol of formula II

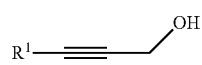

wherein $R^1$ is defined as in formula Ia or Ib, with carbon dioxide in the presence of at least one transition metal catalyst TMC1, which comprises: a transition metal selected from metals of groups 10, 11 and 12 of the periodic table of the elements; and at least one bulky ligand of formula III

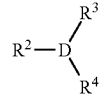

wherein D is P, As or Sb, and $R^2$, $R^3$, and $R^4$ are each independently an organic radical having from 1 to 40 carbon atoms.

\* \* \* \* \*